US008967805B2

(12) United States Patent
Kataoka et al.

(10) Patent No.: US 8,967,805 B2
(45) Date of Patent: Mar. 3, 2015

(54) OPHTHALMOLOGY APPARATUS

(71) Applicants: Hisashi Kataoka, Nagoya (JP); Hiromu Watanabe, Nagoya (JP)

(72) Inventors: Hisashi Kataoka, Nagoya (JP); Hiromu Watanabe, Nagoya (JP)

(73) Assignee: Tomey Corporation, Nagoya (JP)

( * ) Notice: Subject to any disclaimer, the term of this patent is extended or adjusted under 35 U.S.C. 154(b) by 0 days.

(21) Appl. No.: 13/859,082

(22) Filed: Apr. 9, 2013

(65) Prior Publication Data
US 2013/0293839 A1 Nov. 7, 2013

(30) Foreign Application Priority Data

Apr. 11, 2012 (JP) ................................. 2012-090124

(51) Int. Cl.
*A61B 3/14* (2006.01)
*A61B 3/13* (2006.01)
*G06T 7/00* (2006.01)
*G06T 7/40* (2006.01)

(52) U.S. Cl.
CPC ... *A61B 3/14* (2013.01); *A61B 3/13* (2013.01); *G06T 7/0081* (2013.01); *G06T 7/40* (2013.01); G06T 2207/30041 (2013.01)
USPC ....................................................... 351/206

(58) Field of Classification Search
CPC ......... A61B 3/10; A61B 3/107; A61B 3/1005
USPC .................. 351/200–222, 245, 246
See application file for complete search history.

(56) References Cited

U.S. PATENT DOCUMENTS

| 6,276,798 | B1 | 8/2001 | Gil et al. |
| 2005/0186002 | A1 | 8/2005 | Matsutake |
| 2011/0102743 | A1* | 5/2011 | Ihara ............................. 351/206 |
| 2011/0299034 | A1* | 12/2011 | Walsh et al. .................. 351/206 |

FOREIGN PATENT DOCUMENTS

| EP | 1844702 | 10/2007 |
| JP | 2006068110 | 3/2006 |
| JP | 2009254533 | 11/2009 |
| WO | 9201417 | 2/1992 |

OTHER PUBLICATIONS

Uemura, et al., "Specular Microscopy," 1st edition, pp. 71-74, 1990, Nanzando.
English Translation of Abstract of Japanese Patent Application No. JP2006068110.
Machine Translation of Japanese Patent Application No. JP2006068110 prepared by the Japanese Patent Office.
English Translation of Abstract of Japanese Patent Application No. JP2009254533.
Machine Translation of Japanese Patent Application No. JP2009254533 prepared by the Japanese Patent Office.
European Search Report dated Jul. 22, 2013 in European Patent Application No. 13162946.1, 5 pages.

* cited by examiner

*Primary Examiner* — Mahidere Sahle
(74) *Attorney, Agent, or Firm* — Vierra Magen Marcus LLP

(57) ABSTRACT

An ophthalmology apparatus may be provided with an input device, a processor, and an output device. The input device may be configured to input a corneal endothelial cell image to the processor. The corneal endothelial cell image can be obtained by photographing a corneal endothelial cell. The processor may be configured to extract a dark area from the corneal endothelial cell image input by the input device, and to analyze the extracted dark area. The output device may output a result of the analysis by the processor.

14 Claims, 15 Drawing Sheets

Before Integration    After Integration

FIG. 15

| Dark Area | |
|---|---|
| Number | 8 |
| DAD | 1111 /mm$^2$ |
| AVG | 900 $\mu$m$^2$ |
| SD | 100 $\mu$m$^2$ |
| CV | 30 % |
| Max | 990 $\mu$m$^2$ |
| Min | 790 $\mu$m$^2$ |
| Ratio | 9.8% |

| Distribution by Area | | |
|---|---|---|
| 000- 500 $\mu$m$^2$ | 25 % | ▪ |
| 500-1000 $\mu$m$^2$ | 75 % | ▨ |
| 1000- $\mu$m$^2$ | | |

# OPHTHALMOLOGY APPARATUS

CROSS-REFERENCE TO RELATED APPLICATION

This application claims priority to Japanese Patent Application No. 2012-90124 filed on Apr. 11, 2012, the contents of which axe hereby incorporated by reference into the present application.

1. Technical Field

The present teachings relate to an ophthalmology apparatus for analyzing a corneal endothelial cell.

2. Description of Related Art

Japanese Patent Application Publication No. 2009-254533 discloses an analyzing apparatus for analyzing a corneal endothelial cell. In the analyzing apparatus, first a corneal endothelial cell image is displayed on a monitor. If islet noise regions (e.g., a symptom called guttata) are included in the corneal endothelial, cell image, an. operator operates a mouse to exclude the islet noise regions from an analysis target. An arithmetic control unit applies an analysis to the corneal endothelial cell image from which the islet noise regions are removed.

BRIEF SUMMARY OF INVENTION

The guttata is a protrusion formed on a posterior surface of cornea and is caused by Fuchs cornea dystrophy or the like. The guttata itself is not a target of treatment. However, it is expected that useful diagnostic information is obtained from the guttata. For example, according to a degree (a stage) of progress of the guttata, it is possible to predict hypofunction and short life of a corneal endothelial cell.

With a corneal endothelial cell observing apparatus (i.e., a specular microscope), the guttata and the like are observed as dark areas. However, in Japanese Patent Application Publication No. 2009-254533, the dark areas (i.e., islet noise regions including the guttata and the like) included in the corneal endothelial cell image are removed and only the corneal endothelial cell image after the removal is analyzed.

It is an object of the present teachings to provide an ophthalmology apparatus for analyzing the dark areas included in the corneal endothelial cell image.

In one aspect of the present teachings, an ophthalmology apparatus includes an image input unit configured to input a corneal endothelial cell image obtained by photographing a corneal endothelial cell, an extracting unit configured to extract a dark area from the corneal endothelial cell image input by the images input unit, an analyzing unit configured to analyze the dark area extracted by the extracting unit, and an analysis result output unit configured to output an analysis result analyzed by the analyzing unit.

The ophthalmology apparatus extracts the dark area from the corneal endothelial cell image and analyzes the extracted dark image. The ophthalmology apparatus outputs a result obtained by analyzing the dark area. Therefore, it is possible to objectively evaluate the dark area included in the corneal endothelial cell.

In another aspect of the present teachings, a program for analyzing a corneal endothelial cell image obtained by photographing a corneal endothelial cell is provided. The program causes a computer to execute extracting a dark area from the corneal endothelial cell image, analyzing the dark area extracted by the extracting, and outputting an analysis result analyzed by the analyzing.

BRIEF DESCRIPTION OF DRAWINGS

FIG. 15 is an example of an analysis result (an analysis result of the dark area) displayed on a monitor.

DETAILED DESCRIPTION OF INVENTION

In one aspect of the present teachings, an ophthalmology apparatus may include an analyzing unit configured to calculate data concerning the number of extracted dark areas, data concerning an area of the dark areas, or both the data concerning the number of the extracted dark areas and the data concerning the area of the dark areas. With such a configuration, it is possible to quantitatively evaluate the dark areas and appropriately diagnose a state of a corneal endothelial cell.

In another aspect, of the present teachings, an analysis result output unit may include a display device. In this case, the display device may superimpose and display the dark area extracted by an extracting unit on the corneal endothelial cell image. With such a configuration, it is possible to visually check a state of a distribution of the dark areas.

In another aspect of the present teachings, the extracting unit may remove a non-analysis-target region in the corneal endothelial cell image and extract the dark area from the corneal endothelial cell image from which the non-analysis-target region is removed. With such a configuration, since the dark areas are extracted after the non-analysis-target region is removed from the corneal endothelial cell image, it is possible to efficiently extract the dark areas from the corneal endothelial cell image.

In another aspect of the present teachings, the extracting unit may extract one or a plurality of local minimum points where a gray level is local minimum by scanning the corneal endothelial cell image, from which the non-analysis-target region is removed, along a first scanning line extending in a first direction. The extracting unit may scan, for each of the extracted local minimum points, the corneal endothelial cell image along a second scanning line extending in a second direction, which passes the local minimum point, and, when the gray level is local minimum at the local minimum point on the second scanning line as well, extract the local minimum point as a bottom point of a dark area candidate. With such a configuration, a point where the gray level is local minimum in the first direction and the second direction is extracted as a bottom point of a dark area candidate. As a result, it is possible to suppress misdetection of a dark area.

In another aspect of the present teachings, the extracting unit may determine, for each of the local minimum points extracted as the bottom point of the dark area candidate, a boundary of the dark area candidate on the basis of a change in the gray level at points on line segments extending radially from the local minimum point. With such a configuration, since the boundary of the dark area candidate is determined with reference to the extracted bottom point of the dark area candidate it is possible to appropriately determine a boundary of the dark area.

(Embodiment)

Figure 1:
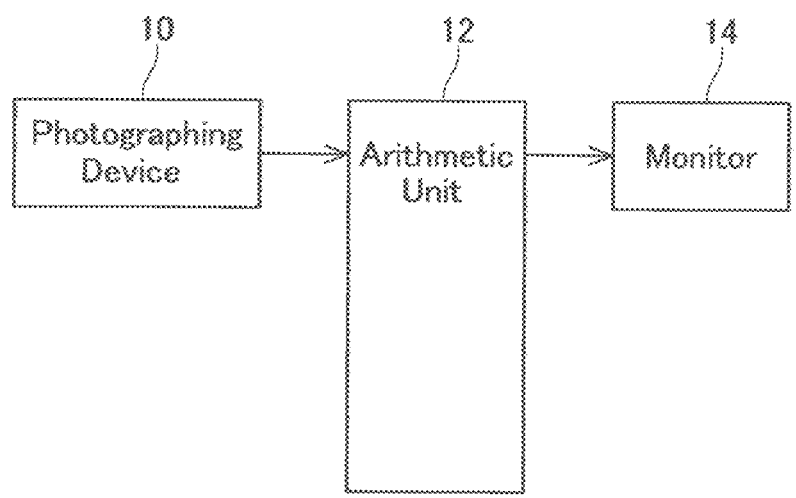
FIG. 1 is a schematic configuration diagram of an ophthalmology apparatus according to an embodiment.

As shown in FIG. 1, an ophthalmology apparatus according to a representative embodiment of the present teachings includes a photographing device 10 configured to photograph a corneal endothelial cell, an arithmetic unit 12 configured to analyze an image of the corneal endothelial cell (hereinafter referred to as corneal endothelial cell image) photographed by the photographing device 10, and a monitor 14 configured to display an analysis result by the arithmetic unit 12.

The photographing device 10 is a so-called specular microscope and is a device for photographing a corneal endothelial cell. The photographing device 10 includes an illumination optical system configured to irradiate slit light on an eye to be examined and a photographing optical system configured to photograph a reflected image of the slit light reflected by the eye. The illumination optical system has an optical axis extending obliquely to the eye and irradiates the slit light obliquely on the eye. The photographing optical system has an optical axis extending obliquely to the eye. An image pickup element (e.g., a CCD element) is disposed on the optical axis. The photographing optical system leads the reflected image of the slit light reflected by the eye to the image pickup element. The image pickup element photographs the slit image. Consequently, a corneal endothelial cell image of the eye is photographed. For the photographing device 10, a conventionally publicly-known configuration (e.g., a configuration disclosed in Japanese Patent Application Publication No. 2006-68110, contents of which are hereby incorporated by reference) can be adopted.

Figure 4:
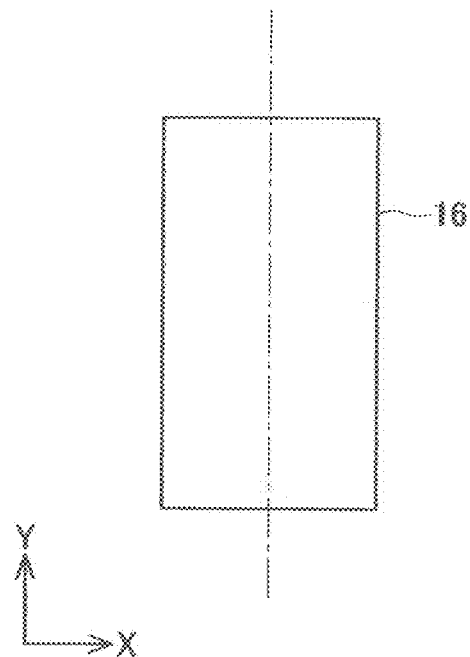
FIG. 4 is a diagram for explaining a corneal endothelial cell image photographed by a photographing device.
Figure 5:
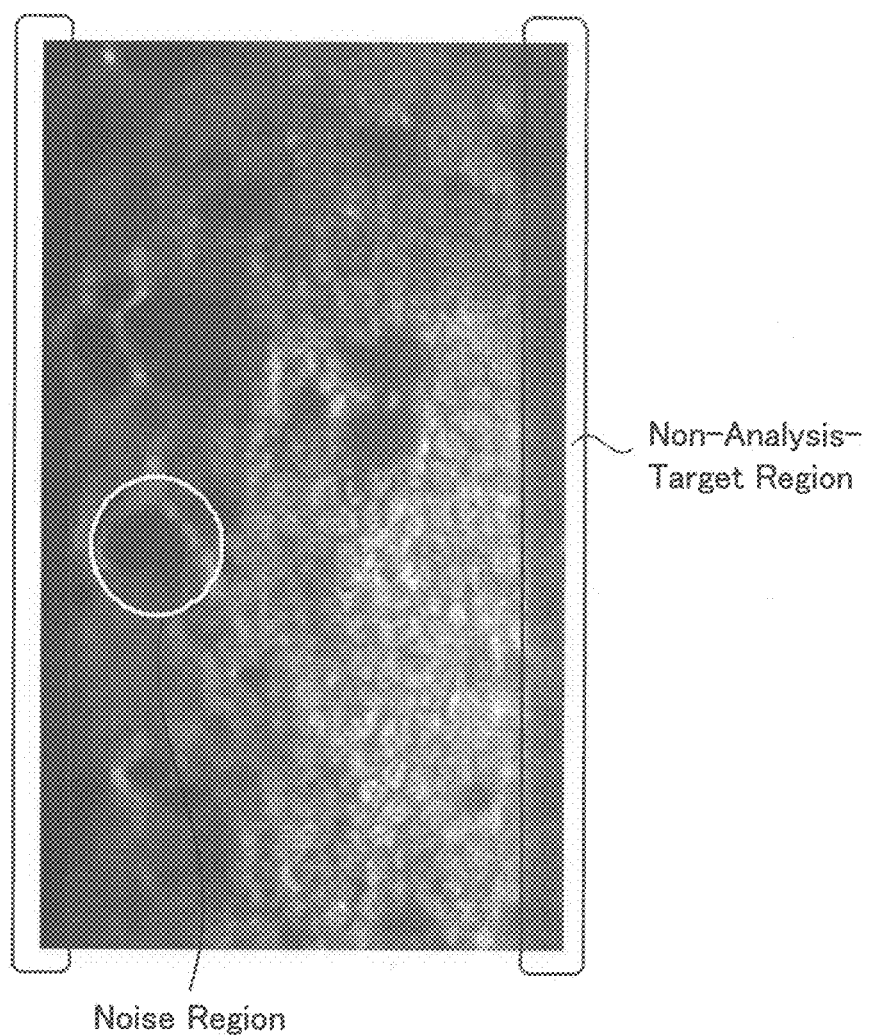
FIG. 5 is a diagram showing the corneal endothelial cell image and a non-analysis-target region included is the image.

As explained above, the photographing device 10 irradiates the slit light obliquely on the eye and photographs the reflected image of the slit light to photograph the corneal endothelial cell image of the eye. Therefore, as shown in FIGS. 4 and 5, a corneal endothelial cell image 16 photographed by the photographing device 10 has a rectangular shape, length in an x-axis direction of which is shorter than length in a y-axis direction thereof. According to a characteristic of an optical system that the slit light is irradiated obliquely on the eye to photograph the eye, a region (a non-analysis-target region) where the corneal endothelial cell is not shown is formed on both left and right sides of the corneal endothelial cell image 16 (i.e., a region present on both sides in the x-axis direction in FIG. 4 and surrounded by a square shown in FIG. 5). The photographing device 10 inputs the photographed corneal endothelial eel image 16 to the arithmetic unit 12.

The arithmetic unit 12 is configured by a computer circuit or a system including at least a CPU, a ROM, and a RAM. The arithmetic unit 12 executes a program stored in a memory to apply analysis processing to the corneal endothelial cell image 16 input from the photographing device 10. That is, the corneal endothelial cell image 16 has the non-analysis-target region and an analysis target, region where the corneal endothelial cell is shown. The analysis target region (i.e., a region obtained by removing the non-analysis-target region on both the left and right sides from the corneal endothelial cell image 16) includes a noise region (e.g., a portion surrounded by a circle shown in FIG. 5) due to guttata or the like. Therefore, the arithmetic unit 12 applies corneal endothelial cell analysis processing (e.g., for extracting a contour of a corneal endothelial cell and applying statistic processing to the extracted corneal endothelial cell) to the region from which the noise region included in the analysis target region is excluded. The arithmetic unit 12 applies dark area analysis processing (explained in detail below) to a dark area extracted from the noise region in the analysis target region. Since the corneal endothelial cell analysis processing is conventionally publicly-known analysis processing, in this specification, detailed explanation of the corneal endothelial cell processing is omitted.

The monitor 14 is connected to the arithmetic unit 12 via a communication line. The monitor 14 displays an image on the basis of a signal output from the arithmetic unit 12. For example, the corneal endothelial cell image photographed by the photographing device 10, a result of the analysis performed by the arithmetic unit 12, and the like are displayed on the monitor 14.

Figure 2:
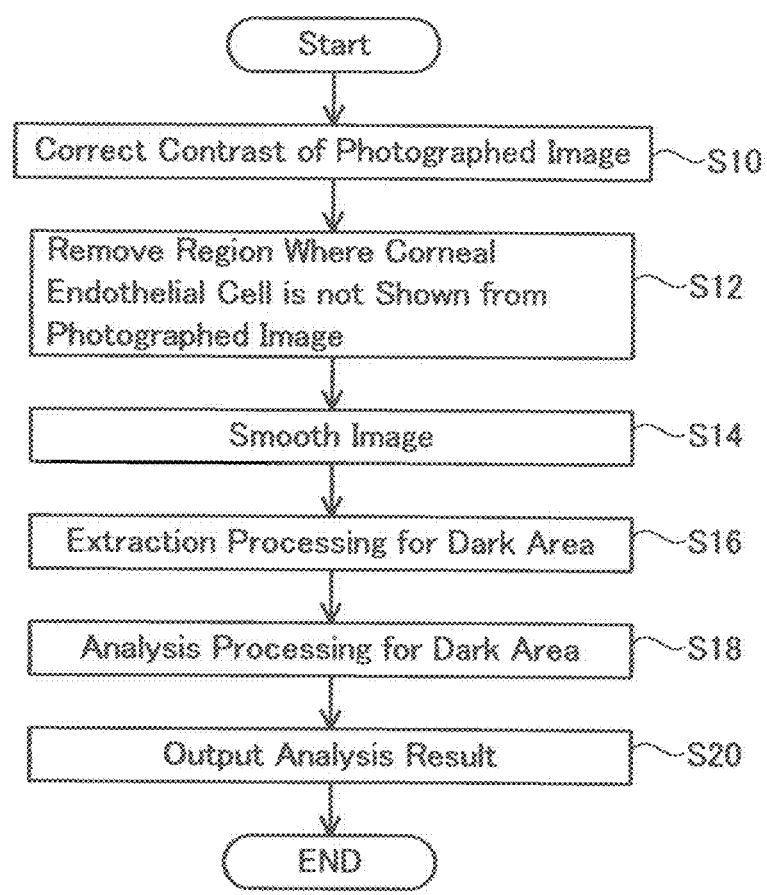
FIG. 2 is a flowchart for explaining a procedure of processing executed by an arithmetic unit of the ophthalmology apparatus according to the embodiment.

A procedure for analyzing a corneal endothelial cell image executed by the arithmetic unit 12 will be explained. When a corneal endothelial cell image photographed by the photographing device 10 is input to the arithmetic unit 12, the arithmetic unit 12 executes the analysis processing shown in FIG. 2 on the input corneal endothelial cell image. As shown in FIG. 2, first, the arithmetic unit 12 performs contrast correction for the input corneal endothelial cell image (S10). That is, in the corneal endothelial cell image in which a corneal endothelial cell is shown, as shown in FIG. 5, a contour line of the corneal endothelial cell has a dark color and an inside of the contour line has a bright color. Therefore, when the corneal endothelial cell is shown in the corneal endothelial cell image, if a change in a gray level is observed in an arbitrary direction, local maximum values and local minimum values alternately appear in a waveform of the change in the gray level (see FIGS. 9 and 10, etc.). Since size of the corneal endothelial sell usually does sot substantially change, waves having similar shapes are repeated. Therefore, first, the arithmetic unit 12 uniformalizes a base and a maximum value of a gray level of the entire input corneal endothelial cell image (i.e., performs contrast correction). Consequently, the waveform of the change in the gray level observed in the arbitrary direction is a waveform, levels of the local maximum values and the local minimum values are not substantially different.

Figure 6:
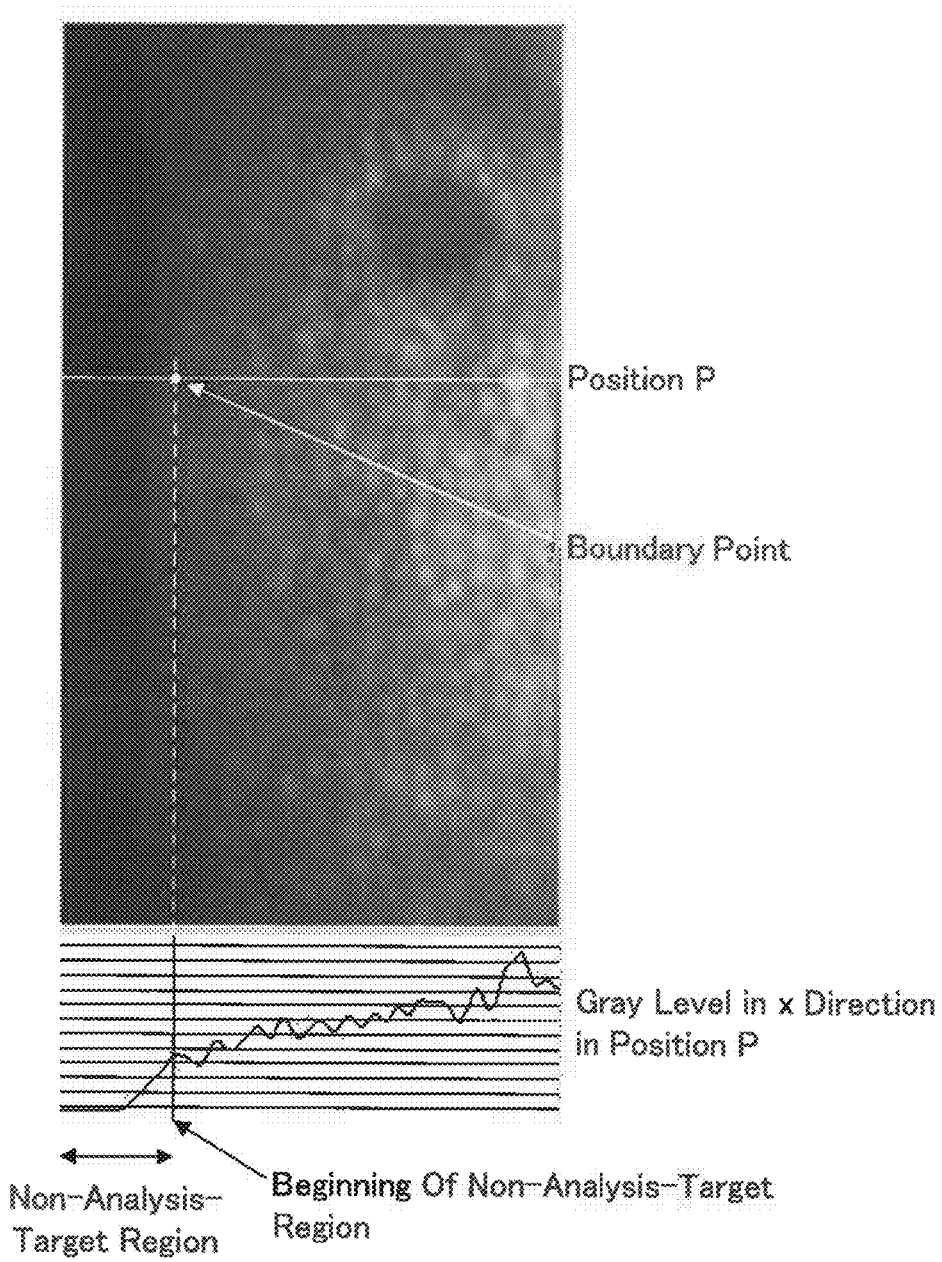
FIG. 6 is a diagram (1) for explaining processing for setting a boundary line of the non-analysis-target region from the corneal endothelial sell image.
Figure 7:
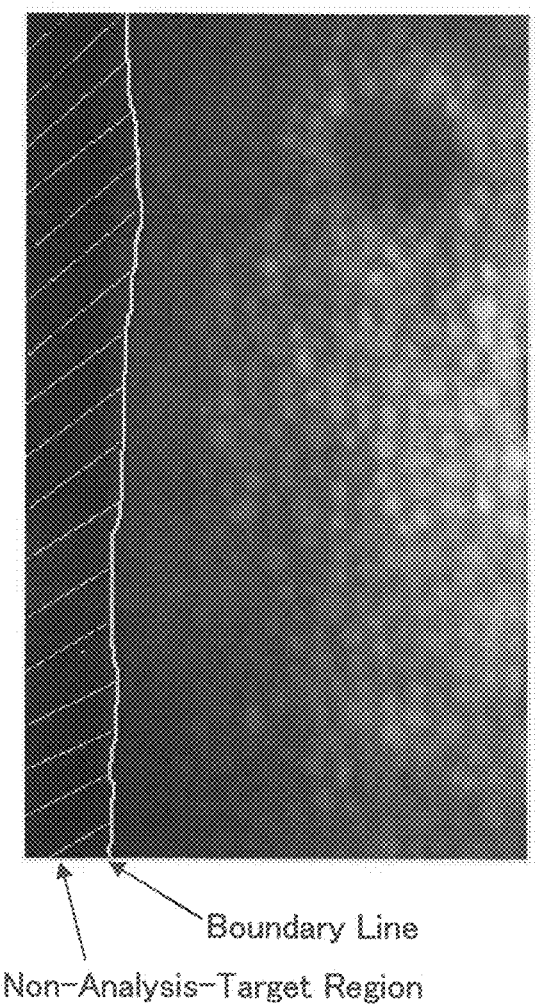
FIG. 7 is a diagram (2) for explaining the processing for setting a boundary line of the non-analysis-target region from the corneal endothelial cell image.
Figure 8:
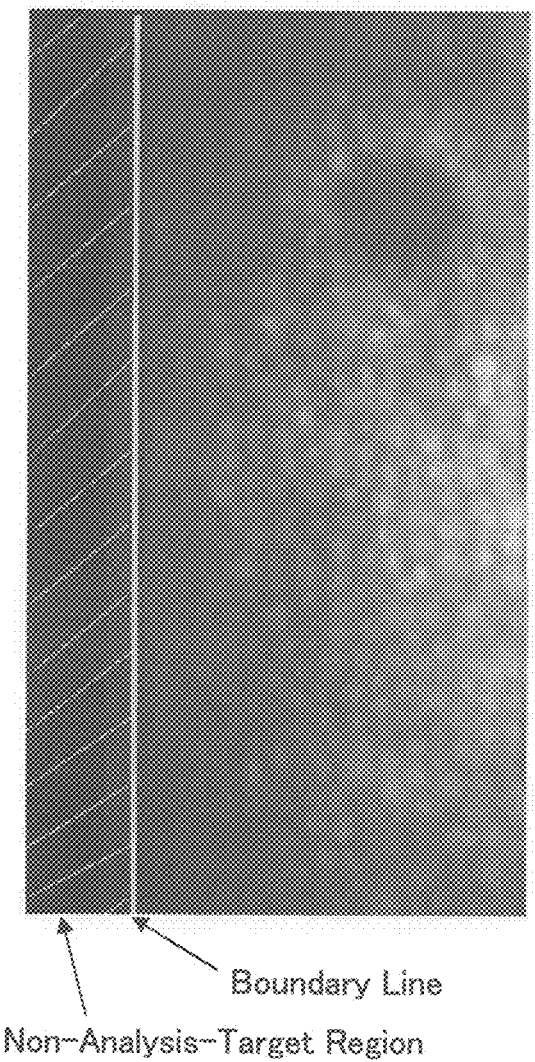
FIG. 8 is a diagram (3) for explaining the processing for setting a boundary line of the non-analysis-target region from the corneal endothelial cell image.

Subsequently, the arithmetic unit 12 removes a region where the corneal endothelial cell is not shown (i.e., a non-analysis-target region) from the corneal endothelial cell image subjected to the contrast correction (S12). As a specific procedure, first the arithmetic unit 12 applies filter processing to the corneal endothelial cell image to remove noise and adjusts contrast of the entire image to be uniform. When cross sections of the image are taken along a horizontal direction and a vertical direction and a change in a gray level of the image is observed, the gray level is high (bright) in the cell and low (dark) in the cell contour. In a waveform of the gray level, high and low alternately appear (see the gray level in a position P in FIG. 6). Subsequently, the arithmetic unit 12 performs scanning in the horizontal direction, extracts a position in a lateral direction (an X direction) where a level difference of waveforms appearing on left and right of the image starts to change a little, and sets a boundary point as a beginning of the non-analysis-target region (see FIG. 6). The arithmetic unit 12 sequentially performs this scanning in the horizontal direction from an upper end to a lower end of the image. The arithmetic unit 12 sets a boundary line of the non-analysis-target region from boundary points obtained from the scanning of the entire image (see FIG. 7). Alternatively, the arithmetic unit 12 may comprehensively determine a boundary line from the boundary points obtained from the scanning of the entire image and set a linear boundary line in a longitudinal direction (a Y direction) (see FIG. 8). In this case, since a scanning start point is uniform during dark area extraction in step S16, extracting process is facilitated. In determination of a boundary of the non-analysis-target region and the analysis target region, for example, a position where wave height (e.g., a difference between a local maximum value and a local minimum value) and the number of waves (e.g., the number of waves in a certain determined number of pixels) of the waveform of the gray level fall below certain appropriate setting values can be regarded as a position where the gray level starts to steeply change (i.e., a beginning of the analysis target region). By removing the non-analysis-target region from the corneal endothelial cell image in this way, it is possible to appropriately and efficiently perform processing in step S14 and subsequent steps.

Subsequently, in order to remove local noise included in the corneal endothelial cell image, the arithmetic unit 12 performs smoothing processing for the corneal endothelial cell image (S14). For the smoothing processing, a filter having a function for, is a region where the gray level steeply changes, making it possible to retain the change sad further emphasize the change is applied. By the smoothing processing, the local noise is removed and the gray level of a region where the gray level is low (a noise region (a dark area candidate)) is substantially reduced. As a result, a change in the gray level of a boundary portion of the noise region (i.e., the dark area candidate) becomes steep. Note that, in the smoothing processing in step S14, the smoothing filter may be applied a plurality of times.

Figure 3:
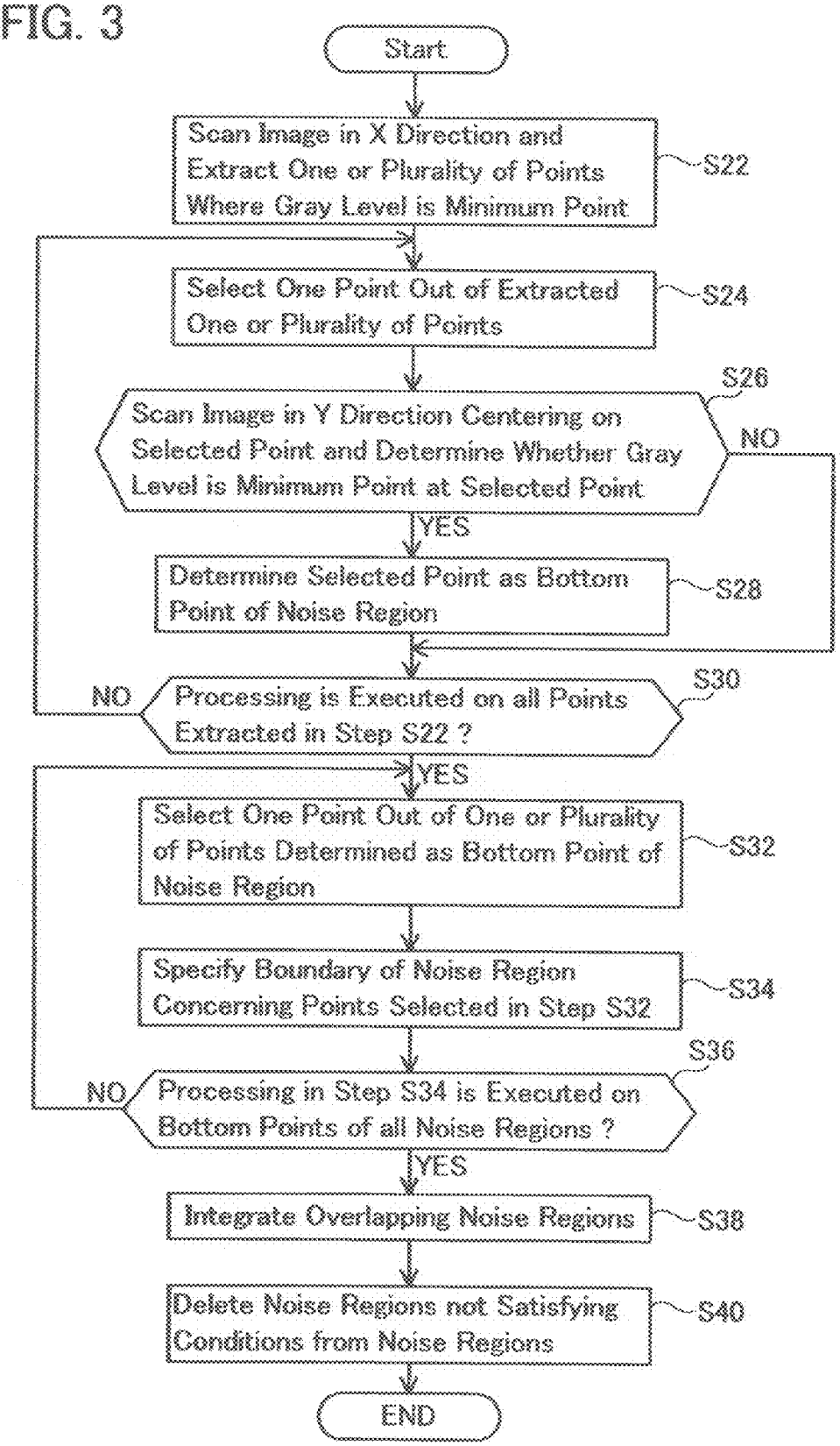
FIG. 3 is a flowchart for explaining a procedure of extraction processing for a dark area (step 16 in FIG. 2).
Figure 9:
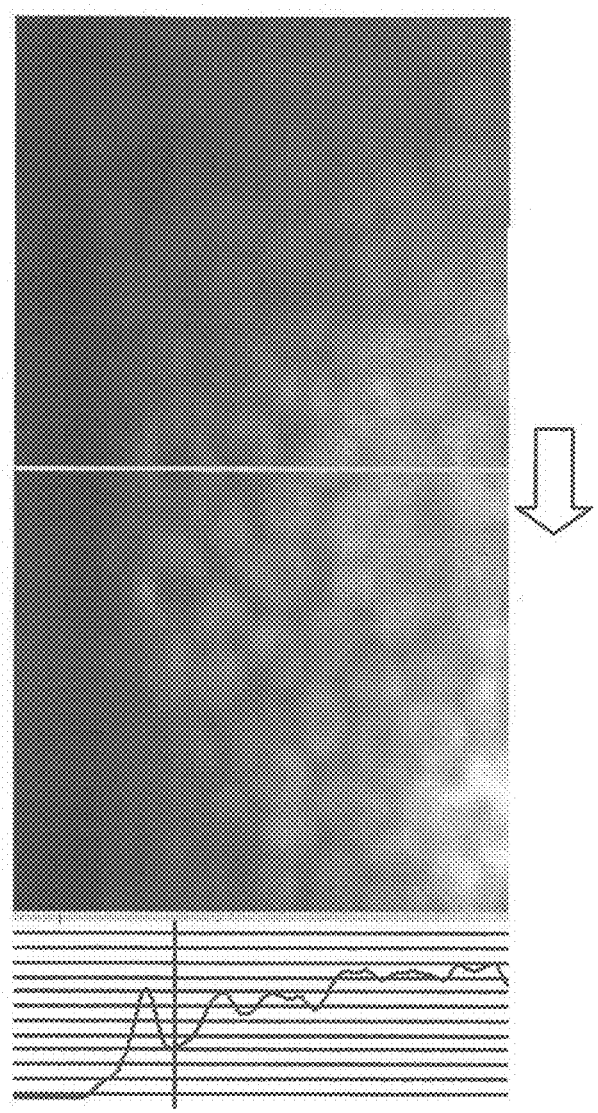
FIG. 9 is a diagram showing the corneal endothelial cell image and a change in a gray level along an x-direction scanning line shown in the corneal endothelial cell image.

Subsequently, the arithmetic unit 12 performs processing for extracting a dark area from the corneal endothelial cell image (S16). The processing in step S16 will be explained in detail with reference to FIG. 3. As shown in FIG. 3, the arithmetic unit 12 scans the corneal endothelial cell image in the x-axis direction and extracts one or a plurality of points where the gray level is a local minimum point (S22). Specifically, as shown in FIG. 9, the arithmetic unit 12 extracts, from a waveform of the gray level on the seaming line extending in the x-axis direction in the corneal endothelial cell image, a position where the gray level is a local minimum point in the waveform. The arithmetic unit 12 applies this processing to the entire corneal endothelial cell image from the upper end to the lower end.

Figure 10:
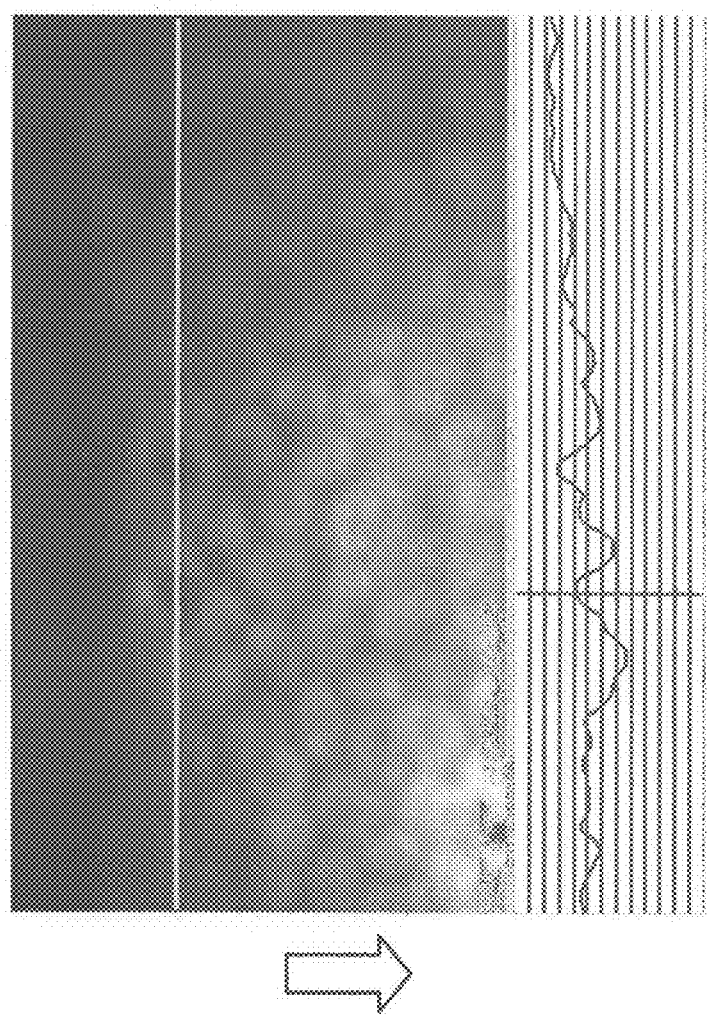
FIG. 10 is a diagram showing the corneal endothelial cell image and a change in a gray level along a y-direction scanning line shown in the corneal endothelial cell image.

Subsequently, the arithmetic unit 12 selects one point out of the one or the plurality of points extracted in step S22 (S24), scans the corneal endothelial cell image in the y-axis direction centering on the point, and determines whether the gray level is a local minimum point, at the selected point (S26). Specifically, as shown in FIG. 10, the arithmetic unit 12 determines, from a waveform of the gray level on a scanning line extending in the y-axis direction passing the selecting point, whether the selected point is a local minimum value in the waveform.

When the gray level is the local minimum point at the selected point in the y-axis direction as well (YES in step S26), the arithmetic unit 12 determines the selected point as a bottom point of the noise region (i.e., the dark area candidate) (S28). On the other hand, when the gray level is not the local minimum point at the selected point in the y-axis direction (NO in step S26), the arithmetic unit 12 skips step S28 and proceeds to step S30. Consequently, the point where the gray level is local minimum only in the x-axis direction is removed and only the point where the gray level is local minimum both in the x-axis direction and the y-axis direction is selected as the bottom point of the noise region.

When proceeding to step S30, the arithmetic unit 12 determines whether the processing in steps S26 and S28 are executed on all the points extracted in step S22. When the processing is not executed on all the extracted points (NO in step S30), the arithmetic unit 12 returns to step S24 and executes the processing from step S24. Consequently, the processing in steps S26 and S28 is executed on all the points extracted in step S22. On the other hand, when the processing is executed on all the extracted points (YES in step S30), the arithmetic unit 12 proceeds to step S32.

Figure 11:
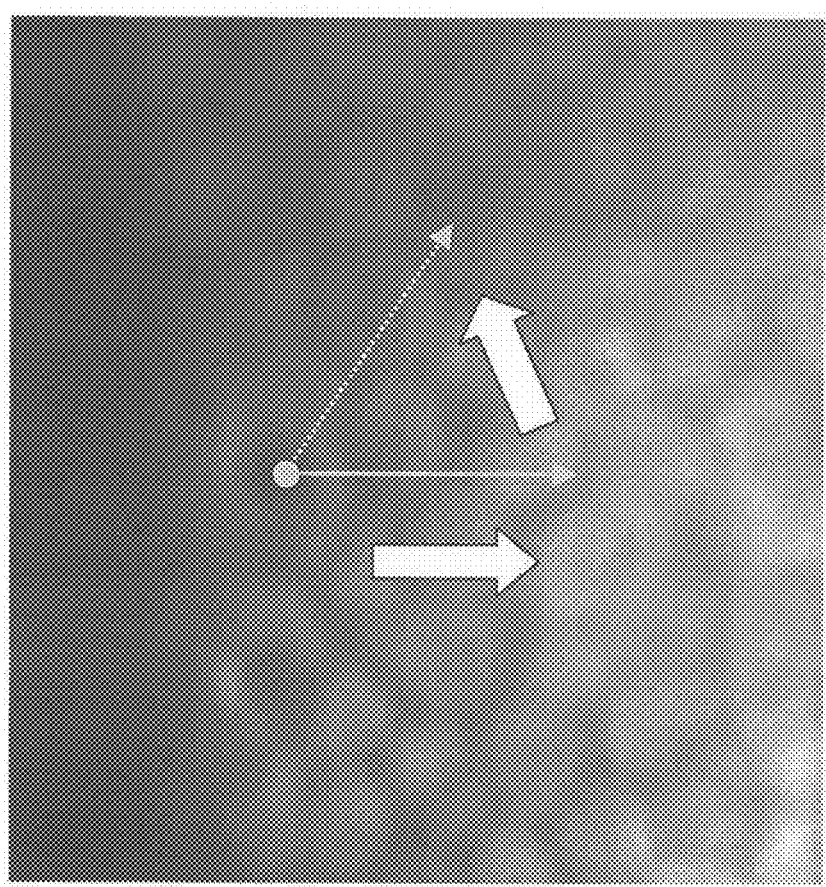
FIG. 11 is a diagram (1) for explaining processing for determining a boundary of the dark area.
Figure 12:
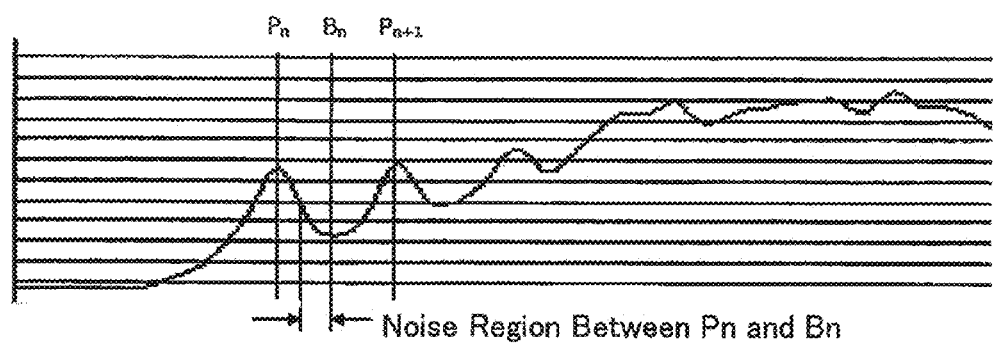
FIG. 12 is a diagram (2) for explaining the processing for determining a boundary of the dark area.

When proceeding to step S32, the arithmetic unit 12 selects one point from the one or the plurality of points determined as the bottom points of the noise region in step S28 and specifies a boundary of the noise region (i.e., the dark area candidate) concerning the point (S34), A procedure for determining the boundary of the noise region will be explained. First, as shown in FIG. 11, the arithmetic unit 12 rotates a line segment having predetermined length radially at 360 degrees around the point (i.e., the local minimum point) selected in step S32. Subsequently, the arithmetic unit 12 calculates, for each of radial lines, from a waveform of the gray level of pixels on the radial line, a change in the gray level to a local maximum point located in the vicinity of the selected point (i.e., the local minimum point). Subsequently, the arithmetic unit 12 calculates an average gray level from the gray level of the selected point (i.e., the local minimum point) and the gray level of the local maximum point. The arithmetic unit 12 identifies, as the noise region (i.e., the dark area candidate), a portion where fee gray level is lower than the average gray level in the waveform of the gray level on the radial line. For example, as shown in FIG. 12, when the gray level on the scanning line changes, in specifying a boundary of the noise region (i.e., the dark area candidate) at a local minimum point Bn, first, the arithmetic unit 12 specifies the local minimum point Bn and a local maximum point (e.g., Pn) in the vicinity of the local minimum point Bn. Subsequently, the arithmetic unit 12 calculates an average value $(L_{Pn}+L_{Bn})/2$ of the gray levels at the local minimum point and the local maximum point and determines a region where the gray level is lower than the average value (i.e., a range indicated as a noise region between Pn and Bn in the figure) as the noise region (i.e., the dark area candidate). Since the noise region is determined for each of fee radial lines, in some case, a boundary of the noise region substantially changes in the radial lines adjacent to each other. Therefore, the arithmetic unit 12 smoothes data in a predetermined angle range and deletes the data substantially different from data on the radial lines adjacent to each other. Instead of simply performing the smoothing, the arithmetic unit 12 may calculate a standard deviation in advance and perform smoothing processing after excluding data substantially deviating from a standard deviation value.

Subsequently, the arithmetic unit 12 determines whether the processing is step S34 is executed on all the points extracted in step S30 (S36). When the processing is not executed on all the extracted points (NO in step S36), the arithmetic unit 12 returns to step S32 and executes the processing from step S32. Consequently, the processing in step S30 is executed on all the points extracted in step S30 and the noise region is determined. On the other hand, when the processing is executed on all the extracted points (YES in step S36), the arithmetic unit 12 proceeds to step S38.

Figure 13:
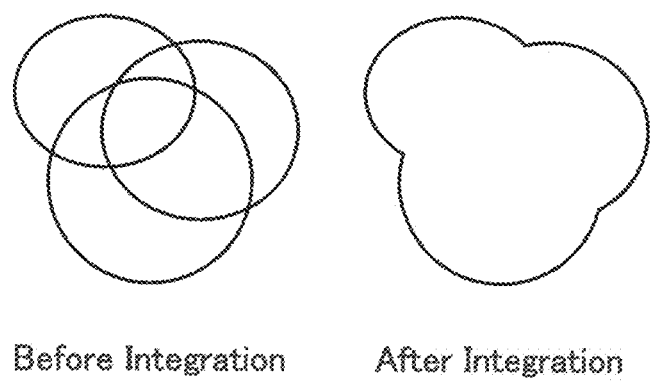
FIG. 13 is a diagram for explaining processing for integrating dark areas.

In step S38, the arithmetic unit 12 integrates the noise regions overlapping one another among the noise regions determined in step S34 (S38). That is, since the processing in step S34 is executed on all the points extracted in step S30, as shown in FIG. 13, in some case, a plurality of noise regions overlap one another. That is, a plurality of local minimum points are present hi one noise region and noise regions determined for the respective local minimum points overlap one another. Therefore, in such a case, the arithmetic unit 12 integrates the overlapping regions into one noise region.

Subsequently, the arithmetic unit 12 determines, for each of the noise regions, whether the noise region is a dark area (S40). That is, even if the extracted noise region is a region with the low gray level, it is also likely that the noise region is not the dark area. Therefore, the arithmetic unit 12 determines whether the extracted noise region is the dark area. For example, when an area of the noise region is smaller than a setting value (e.g., a first setting value) set in advance, since it is likely that the noise region is a shadow in photographing, the arithmetic unit 12 determines that the noise region is not the dark area. Alternatively, when the area of the noise region is smaller than another setting value (e.g., a second setting value) set in advance and an aspect ratio of the noise region exceeds a predetermine value, since it is likely that a contour line of the corneal endothelial cell is misrecognized, the arithmetic unit 12 determines that the noise region is not the dark area. Alternatively, when an edge is unclear, it is likely that the noise region is a portion, having a moderately changing shadow, the arithmetic unit 12 determines that the noise region is not the dark area. Alternatively, when the area of the noise region is a medium size (i.e., the first setting value<the area<the second setting value) and a periphery of the noise area is not surrounded by a plurality of local maximum points, since it is likely that the noise region is not a noise region on the corneal endothelial cell, the arithmetic unit 12 determines that the noise region is not the dark area. The arithmetic unit 12 determines (extracts) a noise region corresponding to none of these exclusion conditions as the dark area.

When the dark area is extracted, returning to step S18 in FIG. 2, the arithmetic unit 12 applies analysis processing to the extracted dark area (S18). That is, the number of dark areas included in the corneal endothelial cell, an average area of the dark areas, a standard deviation of areas of the dark areas, and the like are calculated. Subsequently, the arithmetic unit 12 outputs a result of the analysis processing performed in step S18 to the monitor 14 (S20).

Figure 14:
FIG. 14 is a diagram showing a corneal endothelial cell image and a dark area extracted from the image in a superimposed state.

An example of as image displayed on the monitor 14 will be explained. As shown in FIG. 14, the dark areas are displayed on the monitor 14 while being superimposed on the corneal endothelial cell image. Consequently, it is possible to visually grasp a state of a distribution of the dark areas. As shown in FIG. 15, a table and a graph of a result obtained by subjecting the dark areas are displayed, on the monitor 14. In the table, "Number" indicates the number of dark areas, "DAD" indicates density [number/mm$^2$] of the dark areas, "AVG" indicates an average area [μm$^2$] of the dark areas, "SD" indicates a standard deviation [μm$^2$] of areas of the dark areas, "CV" indicates a fluctuation coefficient (i.e., a number obtained by dividing the standard deviation by the average value) of the areas of the dark areas, "Max" indicates a maximum area [μm$^2$] of the dark areas, "Min" indicates a minimum area [μm$^2$] of the dark areas, and "Ratio" indicates an area of the dark areas/(a corneal endothelial cell area+the area of the dark areas).

In the ophthalmology apparatus according to this representative embodiment, a dark area is extracted from the corneal endothelial cell image and the extracted dark area is analyzed. A result obtained by analyzing the dark area is output. Therefore, it is possible to objectively and quantitatively evaluate dark areas included in the corneal endothelial cell. As a result, it is possible to appropriately diagnose a state of a corneal endothelium of the eye.

For example, since the dark areas can be quantitatively evaluated, it is possible to quantitatively perform stage classification of the dark areas. Since follow-up study of the number of dark areas and areas of the dark areas can be quantitatively performed, it is possible to predict hypofunction and short life of the corneal endothelial cell. It is also possible to predict effects before and after medical treatment when a remedy for discharging moisture from a cornea is performed or a drug is administered. Further, when a visual loss is involved due to a spread of guttata to a wide range, it is possible to objectively evaluate a degree of the visual loss by using the analysis data of the dark areas. Further, in a preoperative informed consent of a cataract surgery, when dark areas are found in a corneal endothelial cell of a patient, it is possible to inform the patient beforehand of, is addition to hypofunction due to the surgery, for example, occurrence of inadequacy due to guttata involved in aging.

Further, in the ophthalmology apparatus according to this representative embodiment, dark areas are extracted from the corneal endothelial cell image. Therefore, an analysis of the corneal endothelial cell can be applied to a region excluding the dark areas. As a result, it is possible to prevent misdetection of a contour line of the corneal endothelial cell and realize an increase in speed of processing.

While specific examples of the present teachings have been described above in detail, these examples are merely illustrative and place no limitation on the scope of the patent claims. The technology described in the patent claims also encompasses various changes and modifications to the specific examples described above.

For example, in the embodiment explained above, the corneal endothelial cell image is input from the photographing device 10 to the arithmetic unit 12. However, the present teachings are not limited to such an example. For example, a corneal endothelial cell image photographed by another specular microscope may be input to an arithmetic unit via as input device. In this case, an input/output circuit for inputting data to the arithmetic unit is the "image input unit".

The technical elements explained in the present description or drawings provide technical utility either independently or through various combinations. The present invention is not limited to the combinations described at the time the claims are filed. Further, the purpose of the examples illustrated by the present description or drawings is to satisfy multiple objectives simultaneously, and satisfying any one of those objectives gives technical utility to the present invention.

What is claimed is:

1. An ophthalmology apparatus comprising:
an input device configured to input a corneal endothelial cell image obtained by irradiating a slit light obliquely on an eye to be examined and photographing a reflected image of the slit light from a corneal endothelial cell of the eye;
a processor configured to extract a dark area from the corneal endothelial cell image input by the input device, and to analyze the extracted dark area, wherein the processor is configured to determine a boundary of the dark area on the basis of a change in a grey level of the corneal endothelial cell image; and
an output device configured to output a result of the analysis by the processor.

2. The ophthalmology apparatus according to claim 1, wherein the processor calculates data concerning a number of extracted dark areas, data concerning an area of the dark areas, or both the data concerning the number of the extracted dark areas and the data concerning the area of the dark areas.

3. The ophthalmology apparatus according to claim 2, wherein
the output device includes a display device, and
the display device superimposes and displays the dark area extracted by the processor on the corneal endothelial cell image input by the input device.

4. The ophthalmology apparatus according to claim 3, wherein
the processor is configured to remove a non-analysis-target region in the corneal endothelial cell image and to extract the dark area from the corneal endothelial cell image from which the non-analysis-target region is removed.

5. The ophthalmology apparatus according to claim 4, wherein
the processor is configured to extract one or a plurality of local minimum points where a gray level is local minimum by scanning the corneal endothelial cell image, from which the non-analysis-target region is removed, along a first scanning line extending in a first direction,
the processor is configured to scan, for each of the extracted local minimum points, the corneal endothelial cell image along a second scanning line extending in a second direction, which passes the local minimum point, and,
when the gray level is local minimum at the local minimum point on the second scanning line as well, the processor is configured to extract the local minimum point as a bottom point of a dark area candidate.

6. The ophthalmology apparatus according to claim 5, wherein the processor determines, for each of the local minimum points extracted as the bottom point of the dark area candidate, a boundary of the dark area candidate on the basis of a change in the gray level at points on line segments extending radially from the local minimum point.

7. The ophthalmology apparatus according to claim 1, wherein
the processor is configured to remove a non-analysis-target region in the corneal endothelial cell image and to extract the dark area from the corneal endothelial cell image from which the non-analysis-target region is removed.

8. The ophthalmology apparatus according to claim 7, wherein
the processor is configured to extract one or a plurality of local minimum points where a gray level is local minimum by scanning the corneal endothelial cell image, from which the non-analysis-target region is removed, along a first scanning line extending in a first direction,
the processor is configured to scan, for each of the extracted local minimum points, the corneal endothelial cell image along a second scanning line extending in a second direction, which passes the local minimum point, and,
when the gray level is local minimum at the local minimum point on the second scanning line as well, the processor is configured to extract the local minimum point as a bottom point of a dark area candidate.

9. The ophthalmology apparatus according to claim 8, wherein the processor determines, for each of the local minimum points extracted as the bottom point of the dark area candidate, a boundary of the dark area candidate on the basis of a change in the gray level at points on line segments extending radially from the local minimum point.

10. An ophthalmology apparatus comprising:
a specular microscope configured to photograph a corneal endothelial cell of an eye to be examined;
a processor configured to extract a dark area from the corneal endothelial cell image input by the specular microscope, and to analyze the extracted dark area, wherein the processor is configured to determine a boundary of the dark area on the basis of a change in a grey level of the corneal endothelial cell image; and
a display configured to display the dark area extracted by the processor on the corneal endothelial cell image input by the specular microscope.

11. The ophthalmology apparatus according to claim 10, wherein
the processor calculates data concerning a number of extracted dark areas, data concerning an area of the dark areas, or both the data concerning the number of the extracted dark areas and the data concerning the area of the dark areas, and
the display device is configured to display the data calculated by the processor.

12. The ophthalmology apparatus according to claim 11, wherein
the processor is configured to extract one or a plurality of local minimum points where a gray level is local minimum by scanning the corneal endothelial cell image along a first scanning line extending in a first direction,
the processor is configured to scan, for each of the extracted local minimum points, the corneal endothelial cell image along a second scanning line extending in a second direction, which passes the local minimum point, and,
when the gray level is local minimum at the local minimum point on the second scanning line as well, the processor is configured to extract the local minimum point as a bottom point of a dark area candidate.

13. The ophthalmology apparatus according to claim 12, wherein the processor determines, for each of the local minimum points extracted as the bottom point of the dark area candidate, a boundary of the dark area candidate on the basis of a change in the gray level at points on line segments extending radially from the local minimum point.

14. A program for analyzing a corneal endothelial cell image obtained by irradiating a slit light obliquely on an eye to be examined and photographing a reflected image of the slit light from a corneal endothelial cell of the eye, the program causing a computer to execute:
extracting a dark area from the corneal endothelial cell image;
determining a boundary of the extracted dark area on the basis of a change in a grey level of the corneal endothelial cell image;
analyzing the dark area extracted by the extracting; and
outputting a result of the analyzing.

* * * * *